US00PP16008P2

(12) United States Plant Patent
Brown

(10) Patent No.: US PP16,008 P2
(45) Date of Patent: Sep. 27, 2005

(54) ***GAURA* PLANT NAMED 'NUGAUWHITE'**

(50) Latin Name: *Gaura lindheimeri*
Varietal Denomination: Nugauwhite

(75) Inventor: Graham Noel Brown, Pennant Hills (AU)

(73) Assignee: NuFlora International, Macquarie Fields (AU)

( * ) Notice: Subject to any disclaimer, the term of this patent is extended or adjusted under 35 U.S.C. 154(b) by 11 days.

(21) Appl. No.: 10/959,774

(22) Filed: Oct. 6, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Gaura* plant named 'Nugauwhite', characterized by its compact and upright plant habit; freely branching growth habit; freely flowering habit; long flowering period; and white-colored flowers.

1 Drawing Sheet

Botanical classification/cultivar designation: *Gaura lindheimeri* cultivar Nugauwhite.

BACKGROUND OF THE INVENTION

The present Invention relates to a new and distinct cultivar of *Gaura* plant, botanically known as *Gaura lindheimeri*, and hereinafter referred to by the cultivar name Nugauwhite.

The new *Gaura* is a product of a planned breeding program conducted by the Inventor in Cobbitty, New South Wales, Australia. The objective of the breeding program is to create new compact and freely-branching *Gauras* with upright plant habit, numerous flowers and attractive flower coloration.

The new *Gaura* originated from a cross-pollination made by the Inventor in December, 1998 of a proprietary selection of *Gaura lindheimeri* identified as code number X98.1.2, not patented, as the female, or seed, parent with a proprietary selection of *Gaura lindheimeri* identified as code number X98.1.1, not patented, as the male, or pollen, parent. The new *Gaura* was selected as a single plant from the resulting progeny of the cross-pollination by the Inventor in December, 2000 in an controlled environment in Cobbitty, New South Wales, Australia.

Asexual reproduction of the new cultivar by terminal cuttings in a controlled environment in Cobbitty, New South Wales, Australia since December, 2000, has shown that the unique features of this new *Gaura* are stable and reproduced true to type in successive generations.

SUMMARY OF THE INVENTION

Plants of the cultivar Nugauwhite have not been observed under all possible environmental conditions. The phenotype may vary somewhat with variations in environment such as temperature and light intensity without, however, any variance in genotype.

The following traits have been repeatedly observed and are determined to be the unique characteristics of 'Nugauwhite'. These characteristics in combination distinguish 'Nugauwhite' as a new and distinct cultivar of *Gaura:*

1. Compact and upright plant habit.
2. Freely branching growth habit.

3. Freely flowering habit.
4. Long flowering period.
5. White-colored flowers.

Plants of the new *Gaura* can be compared to plants of the parent selections. In side-by-side comparisons conducted in Cobbitty, New South Wales, Australia, plants of the new *Gaura* differed from plants of the parent selections in the following characteristics:

1. Plants of the new *Gaura* had white-colored roots whereas plants of the parent selections had pink-colored roots.
2. Plants of the new *Gaura* had white-colored flowers whereas plants of the parent selections had pink-colored flowers.

Plants of the new *Gaura* can also be compared to plants of the *Gaura* cultivar Whirling Butterflies, not patented. In side-by-side comparisons conducted in Cobbitty, New South Wales, Australia, plants of the new *Gaura* differed from plants of the cultivar Whirling Butterflies in the following characteristics:

1. Plants of the new *Gaura* were more compact than plants of the cultivar Whirling Butterflies.
2. Plants of the new *Gaura* were more freely branching than plants of the cultivar Whirling Butterflies.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Gaura*.

The photograph at the top of the sheet is a close-up view of typical flowers of 'Nugauwhite'.

The photograph at the bottom of the sheet comprises a side perspective view of a typical flowering plant of 'Nugauwhite' grown in a container.

DETAILED BOTANICAL DESCRIPTION

The aforementioned photographs and following observations and measurements describe plants grown in Bonsall, Calif. in a polyethylene-covered greenhouse during the winter and spring with day temperatures ranging from 16 to 35° C. and night temperatures ranging from 10 to 21° C. Plants were grown in 15-cm container and had been growing for about eight weeks when the photographs and description were taken. Plants were pinched one time. Color references are made to The Royal Horticultural Society Colour Chart, 1995 Edition, except where general terms of ordinary dictionary significance are used.

Botanical classification: *Gaura lindheimeri* cultivar Nugauwhite.

Parentage:

*Female parent.*—Proprietary selection of *Gaura lindheimeri* identified as code number X98.1.2, not patented.

*Male parent.*—Proprietary selection of *Gaura lindheimeri* identified as code number X98.1.1, not patented.

Propagation:

*Type cutting.*—Vegetative cuttings.

*Time to initiate roots.*—About one to three weeks.

*Time to produce a rooted young plant.*—About four to five weeks.

*Root description.*—Fine, fibrous; freely branching, dense; white in color.

Plant description:

*Form.*—Compact and upright plant habit; inverted triangle; airy and open plant form. Freely branching growth habit with about eight lateral branches per plant. Moderately vigorous growth habit.

*Plant height.*—About 40 cm.

*Plant diameter.*—About 44 cm.

*Lateral branches.*—Length: About 35 cm. Diameter: About 2 mm. Internode length: About 1.4 to 3 cm. Strength: Strong. Texture: Sparsely pubescent. Color: 146A.

*Foliage description.*—Arrangement: Alternate; simple; sessile. Length: About 6 cm. Width: About 1.5 cm. Shape: Linear to narrowly elliptic. Apex: Acute. Base: Clasping. Margin: Entire to shallow sinuate. Texture, upper and lower surfaces: Slightly pubescent; lower surface more pubescent than upper surface. Venation pattern: Pinnate; arcuate. Color: Developing and fully expanded foliage, upper surface: 147A. Developing and fully expanded foliage, lower surface: 147A. Venation, upper and lower surfaces: 148C.

Flower description:

*Flower type and habit.*—Solitary zygomorphic flowers arranged on terminal and axillary spikes; flowers sessile. Flowers persistent. Flowers face mostly outwardly from the stem axis.

*Quantity.*—Freely flowering; terminal panicles with typically about 60 flower buds and open flowers per inflorescence.

*Natural flowering season.*—Long flowering period; plants typically flower from March through November in Southern California; flowering continuous during this period. Plants start flowering about four to six weeks after planting.

*Flower longevity on the plant.*—About three days.

*Fragrance.*—Not detected.

*Inflorescence length.*—About 14 cm; flowers separated about 1 cm.

*Inflorescence diameter.*—About 2.5 cm.

*Flower size.*—Length: About 2.5 cm. Width: About 3.5 cm. Depth: About 2.3 cm.

*Flower buds.*—Length: About 2 cm. Diameter: About 2.5 mm. Shape: Slender, elongated. Color: 144C.

*Petals.*—Quantity/arrangement: Four petals in a single whorl. Length: About 1.8 cm. Width: About 8 mm. Shape: Elongated oblong; claw-like. Apex: Broadly acute. Margin: Entire. Texture, upper and lower surfaces: Smooth, satiny. Color: When opening, upper and lower surfaces: Close to 155A. Fully opened, upper and lower surfaces: Close to 155A.

*Sepals.*—Arrangement/appearance: Single whorl of four sepals; fused at the base. Length: About 1.5 cm. Width: About 1 cm. Shape: Lanceolate. Apex: Acute. Base: Fused. Margin: Entire. Texture, upper and lower surfaces: Pubescent. Color, upper and lower surfaces: 144B to 144C.

*Peduncles.*—Teminal peduncle length: About 13 cm. Axillary peduncle length: About 5 cm. Width: About 1 mm. Angle: Terminal peduncles, upright; axillary peduncles, about 45° from the stem axis. Strength: Moderately strong. Texture: Smooth, glabrous. Color: 147B.

*Reproductive organs.*—Stamens: Quantity per flower: Eight. Anther shape: Linear; slender. Anther length: Less than 1 mm. Anther diameter: About 4 mm. Anther color: 185A. Pollen amount: Scarce. Pollen color: 150D. Pistils: Quantity per flower: One. Pistil length: About 3 cm. Style length: About 1.8 mm. Style color: 157A. Stigma shape: Four-parted. Stigma color: 145B. Ovary color: 144A.

*Fruit/seed.*—Fruit and seed production has not been observed.

Disease/pest resistance: Plants of the new *Gaura* have not been noted to be resistant to pathogens or pests common to *Gaura*.

Temperature tolerance: Plants of the new *Gaura* have been observed to tolerate temperatures from −4 to 43° C.

It is claimed:

1. A new and distinct cultivar of *Gaura* plant named 'Nagauwhite', as illustrated and described.

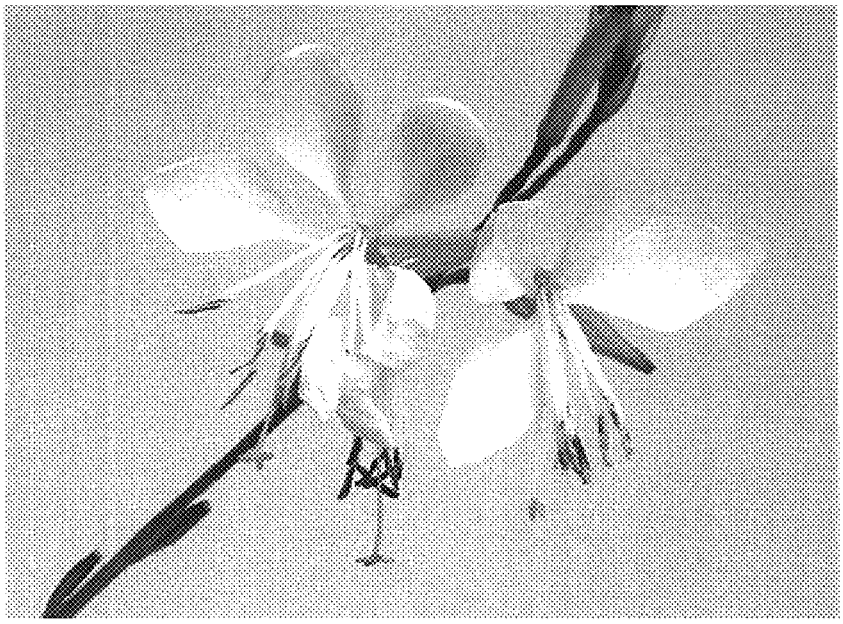
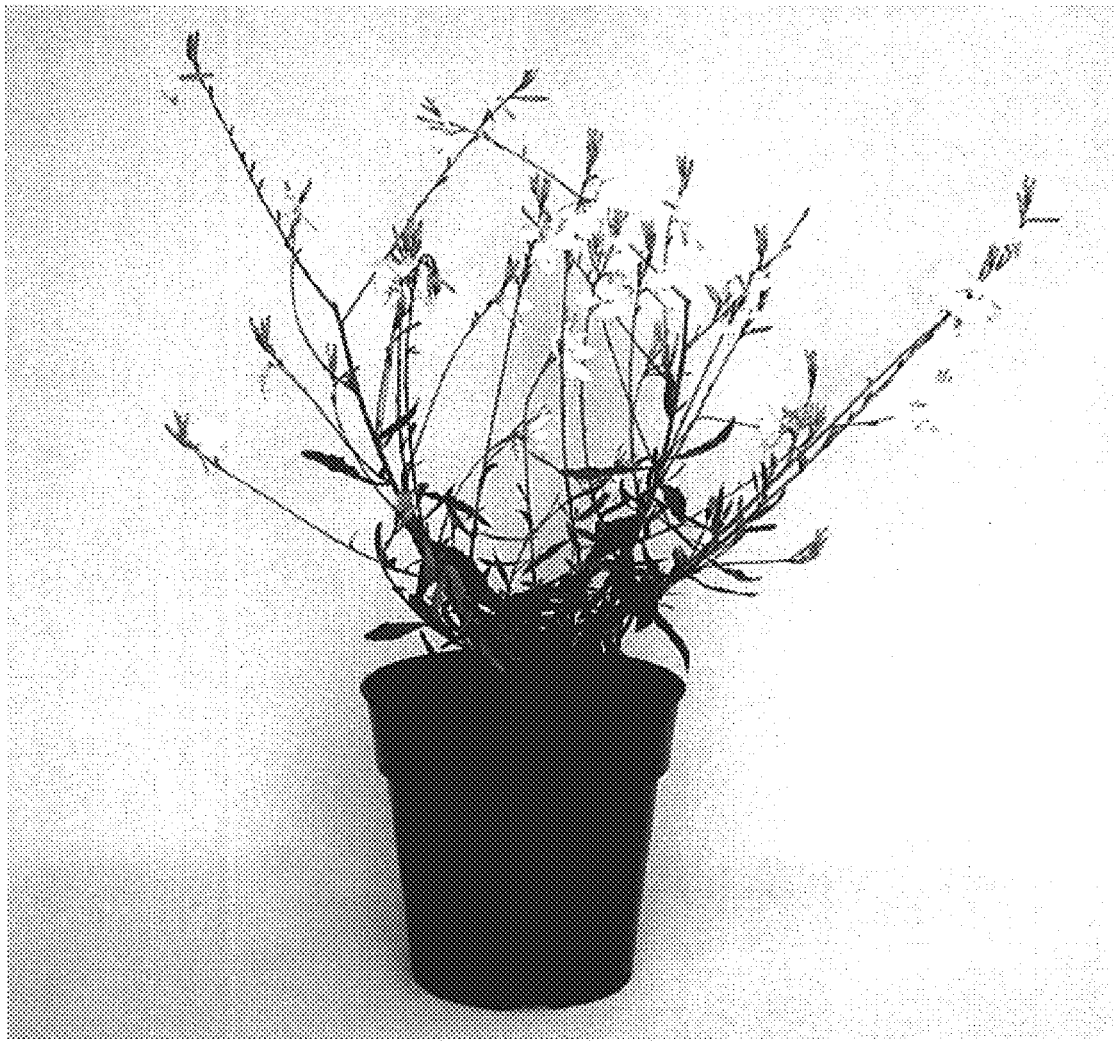

* * * * *